US00PP17686P2

(12) United States Plant Patent
Carruth

(10) Patent No.: US PP17,686 P2
(45) Date of Patent: May 1, 2007

(54) HYBRID TEA ROSE PLANT NAMED 'WEKSUNVOYE'

(50) Latin Name: *Rosa hybrida*
Varietal Denomination: WEKsunvoye

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 11/281,281

(22) Filed: Nov. 17, 2005

(51) Int. Cl.
*A01H 5/00* (2006.01)

(52) U.S. Cl. ..... Plt./132

(58) Field of Classification Search ..... Plt./132
See application file for complete search history.

(56) References Cited

U.S. PATENT DOCUMENTS

PP9,718 P 12/1996 Fryer

*Primary Examiner*—Kent Bell
(74) *Attorney, Agent, or Firm*—McKee, Voorhees & Sease, P.L.C.

(57) ABSTRACT

A new variety of Hybrid Tea rose suitable for garden decoration, having flowers of blended apricot gold with an irregular yellow-colored fan-shaped pattern of venation on the under surface of the petals.

1 Drawing Sheet

Classification: The present invention relates to a new *Rosa hybrida* plant.

Variety denomination: The new plant has the varietal denomination 'WEKsunvoye'.

BACKGROUND OF THE INVENTION

This invention relates to a new and distinct variety of Hybrid Tea Rose. It has as its seed parent the variety known as 'FRYxotic' (U.S. Plant Pat. No. 9,718) and as its pollen parent an undisseminated seeding of Applicant's creation with the following genetic origin (Voodoo×unknown seedling).

SUMMARY OF THE INVENTION

Among the features which distinguish the new variety from other presently available and commercial rose cultivars known to the inventor are the following combination of characteristics: its large flowers of blended apricot gold coloration, its irregular yellow-colored fan-shaped pattern of venation on the under surface of the petals and its many stipitate glands on the surface of the bud. The plant has an upright moderately spreading growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKsunvoye' may be asexually propagated by budding and grafting. The budding and grafting successfully occurred on the plant/rootstock *Rosa hybrida* cv. 'Dr. Huey'.

COMPARISON WITH PARENTS

The new rose may be distinguished from its seed parent, 'FRYxotic' by the following combination of characteristics: whereas 'WEKsunvoye' bears flowers of blended apricot gold with an irregular yellow-colored fan-shaped pattern of venation on the under surface of the petals, 'FRYxotic' bears flowers of apricot pink coloration. The new variety bears flowers with double petalage (about 16 to 28 petals), whereas the seed parent bears flowers with significantly heavier petalage (about 36 to 40 petals). On the spent bloom of the new variety, the petals usually persist, whereas on the spent bloom of the seed parent, the petals usually drop off cleanly.

The new variety may be distinguished from its pollen parent, an undisseminated seedling of Applicant's creation with the following genetic origin (Voodoo×unknown seedling), by the following combination of characteristics: whereas 'WEKsunvoye' bears flowers of blended apricot gold with an irregular yellow-colored fan-shaped pattern of venation on the under surface of the petals, the undisseminated seedling bears flowers of blended orange coloration. 'WEKsunvoye' bears flowers with double petalage (about 16 to 28 petals), whereas the pollen parent bears flowers with significantly lesser petalage (about 8 to 17 petals). The new variety is classified as a hybrid tea rose with an upright moderately spreading mature growing habit, whereas the pollen parent is classified as a floribunda rose with a significantly smaller and more compact mature growing habit.

COMPARISON WITH THE CLOSEST COMMERCIALLY AVAILABLE CULTIVAR

The closest commercially available cultivar to the new variety is the seed parent 'FRYxotic' as described herein.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color references and/or values are based upon the Colour Chart of The Royal Horticultural Society of London, England (1966), except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

BOTANICAL DESIGNATION

The new variety botanical designation is *Rosa hybrida* 'WEKsunvoye'.

FLOWER

The new variety usually bears its flowers singly, sometimes in clusters of two to three per stem. Flowers may be borne in regular rounded clusters on strong short to medium length stems (about 15 to about 50 cm). Outdoors, the plant blooms abundantly and nearly continuously during the growing season. The flowers have a slight tea to fruity fragrance.

BUD

The peduncle is about 2.5 to about 8.2 cm. in length, of somewhat heavy caliper (about 0.4 to about 0.6 cm. in diameter), and usually erect. It is usually moderately smooth but sometimes rough, with some stipitate glands, few hairs and sometimes some small prickles. Peduncle color is between 146C and 146B sometimes lightly suffused, especially on the side exposed to the sun, with between 183C and 187A.

Before the calyx breaks, the bud is about 1.5 to about 2.5 cm. in diameter at the widest point, about 2.0 to about 3.2 cm. in length, and very pointed to somewhat ovoid in shape. The surface of the bud bears many foliaceous appendages and stipitate glands, usually with moderately stout much cut foliaceous parts extending beyond the tip of the bud about ¼ or more of its length. Bud color is between 137C and 146B.

The sepals are about 3.2 to about 4.7 cm. in length and about 1.0 to about 1.6 cm. in width at the widest point. The outer surface color of the sepal is between 137C and 146B. The inner surface color of the sepal is between 137B and 146C and covered with fine wooly tomentum; sepal margins are lined with some stipitate glands and few hairs.

The receptacle of the flower is of somewhat short length (about 0.5 to about 0.7 cm.) and moderately thin in caliper (about 0.7 to about 0.9 cm. in diameter). The receptacle is vase shape in form. Its surface is smooth with some hairs and with thick fleshy walls. The receptacle color is between 146C and 146B.

As the petals open (after the calyx breaks), the bud is about 2.5 to about 4.3 cm. in diameter at the widest point, about 3.4 to about 4.7 cm. in length, and moderately pointed to ovoid in form. The color of the under surfaces of the newly opened petals is between 33C and 47C usually showing an irregular fan shaped pattern of venation of between 13A and 13B in coloration. At the point where the petal attaches, there is a large zone of between 5C and 12B. The color of the upper surfaces of the newly opened petals is between 24B and 24C. At the point where the petal attaches, there is a large zone of between 14A and 14B.

BLOOM

When fully open, the bloom ranges from about 8.7 to about 13.4 cm. in diameter. Petalage is double with about 16 to 28 petals and about 2 to 4 petaloids irregularly arranged. When partially open, the bloom form is somewhat high centered to cupped and the petals are moderately tightly spiraled to cupped to sometimes undulated with petal edges moderately reflexed outward. When fully open, the bloom form is more cupped and the petals are loosely cupped to undulated with petal edges moderately reflexed outward.

PETALS

The substance of the petals is moderately heavy and of medium thickness, with upper surfaces slightly satiny and under surfaces matte. The petals are about 3.0 to about 4.9 cm. in length and about 3.4 to about 5.8 cm. in width at the widest point. Petal margins are entire.

The outer petals are nearly rounded in shape with rounded apices.

The inner petals are moderately obovate in shape with rounded apices.

Petaloids are about 2.4 to about 3.4 cm. in length and about 1.4 to about 3.1 cm. in width at the widest point. Petaloids are irregularly shaped somewhat obovate with rounded apices.

NEWLY OPENED FLOWER

The under surface color of the outer petals is between 41C and 37A usually showing an irregular fan-shaped pattern of venation of between 4B and 12C in coloration. At the point where the petal attaches, there is a large zone of near 5C. The upper surface color of the outer petals is between 28D and 23D. At the point where the petal attaches, there is a large zone of between 9C and 8A.

The under surface color of the intermediate and inner petals is between 33D and 37A usually showing an irregular fan-shaped pattern of venation of between 4B and 12C in coloration. The upper surface color of the intermediate and inner petals is between 28D and 23D.

The under and upper surface color of the petaloids are similar in coloration to the upper and under surfaces of the intermediate and inner petals.

The general tonality of the newly opened flower is between 28D and 23D.

THREE-DAY-OLD FLOWER

The under surface color of the outer petals is between 52D and 49B usually showing an irregular fan-shaped pattern of venation of between 1D and 2C in coloration. At the point where the petal attaches, there is a large zone of between 1D and 2C. The upper surface color of the outer petals is between 27A and 27C sometimes lightly blushed near the petal edge with between 51A and 53D. At the point where the petal attaches, there is a large zone of between 3D and 4C.

The under surface color of the intermediate and inner petals is between 38C and 49B usually showing an irregular fan-shaped pattern of venation of between 4C and 5D in coloration. The upper surface color of the intermediate and inner petals is between 23D and 27C sometimes lightly blushed near the petal edge with between 51A and 53D.

The under and upper surface color of the petaloids are similar in coloration to the upper and under surfaces of the intermediate and inner petals.

The general tonality of the three-day-old flower is between 23D and 27C.

On the spent bloom, the petals usually persist, fading to near 155A.

In October in Upland, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 115) and are arranged regularly about the pistils; a few are mixed with petaloids. The filaments are of medium to long length (about 0.5 to about 1.3 cm.) most with anthers. Filaments are near 3B in color at the base and near 21B in color near the top. The anthers are medium in size for the class and all open approximately at the same time. Anther color is between 14D and 23B when immature and between 200A and 165C at maturity. Pollen is abundant and between 16C and 17D in color.

FEMALE REPRODUCTIVE ORGANS

Pistils vary in number (average about 165). The styles are moderately even, somewhat short in length (about 0.4 to about 0.7 cm.), moderately thin in caliper, and moderately separated. Stigma color is between 12B and 13C. Style color is between 1D and 2D often heavily suffused near the top with near 53A. Ovaries are usually all enclosed in the calyx.

Hips have not been observed on this variety when grown in Upland, Calif.

FOLIAGE

The compound leaves are usually comprised of three to seven leaflets and are borne abundantly. The five-leaflet leaves are about 8.0 to about 14.2 cm. in length and about 6.4 to about 11.7 cm. in width at the widest point, moderately leathery to somewhat crisp in texture, and semi-glossy in finish. The terminal leaflets are about 4.0 to about 8.8 cm. in length and about 2.7 to about 5.7 cm. in width at the widest point, shaped ovate with acute apices and rounded bases. Their margins are usually simply serrate.

The upper surface color of the mature leaf is between 137A and 147A. The under surface color of the mature leaf is between 146B and 147B. The upper surface color of the young leaf is between 146A and 146B, usually heavily suffused with between 187B and 187A. The under surface color of the young leaf is between 146B and 144A, usually heavily suffused with between 187B and 187A.

The rachis is somewhat light to average in caliper and very rough. The upper side is shallowly grooved with some hairs and stipitate glands on the edges of the grooves. The under side of the rachis is very rough with some stipitate glands and small prickles. The rachis color is between 145A and 144A.

The stipules are about 0.8 to about 1.3 cm. in length and of medium width (about 0.4 to about 0.5 cm.) with somewhat short straight points that usually turn out at an angle of more than 45 degrees and sometimes recurve toward the stem. The stipules color is between 146B and 144A.

The petiole is somewhat light to average in caliper and very rough. The upper side is shallowly grooved with some hairs and stipitate glands on the edges of the grooves. The under side of the petiole is very rough with some stipitate glands and small prickles. The petiole is about 0.3 to about 1.6 cm. in length and about 0.1 to about 0.2 cm in diameter at the widest point. The petiole color is between 145A and 144A.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has an upright moderately spreading medium height to tall growing habit (about 140 to about 155 cm. in height and about 58 to about 74 cm. spread at the widest point), with full branching. It displays moderately vigorous growth and the canes are of medium size caliper for the class.

The color of the major stems is between 152B and 146C. They bear many large prickles that are about 0.6 to about 0.9 cm. in length. The large prickles are moderately hooked downward with a long narrow oval base; prickle color is between 166A and 175A. The major stem bears some small prickles of similar shape and coloration.

The color of the branches is between 146A and 146B. They bear many large prickles which are of similar size and shape to the large prickles on the major stems; prickle color is between 162B and 163D sometimes lightly suffused with near 185C. The branches bear some small prickles of similar shape and coloration.

The color of the new shoots is between 146D and 144A sometimes moderately suffused with between 187B and 183B. They bear many large prickles which are of similar size and shape to the large prickles on the major stems; prickle color is between 160C and 162C usually suffused with between 187C and 183C. The shoots bear some small prickles of similar shape and coloration.

I claim:

1. A new and distinct Hybrid Tea rose plant of the variety substantially as described and illustrated herein.

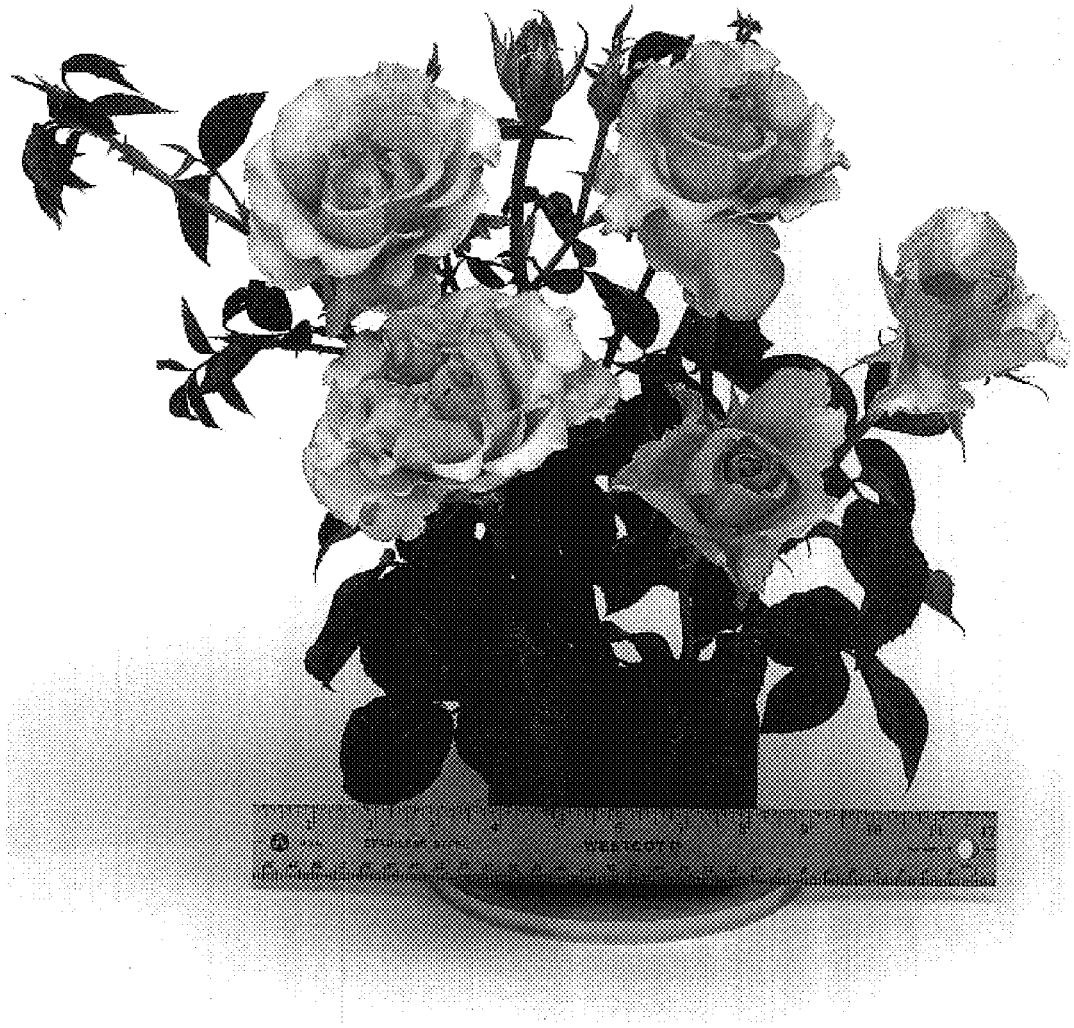

* * * * *